United States Patent [19]

Bridge et al.

[11] Patent Number: 5,063,206

[45] Date of Patent: Nov. 5, 1991

[54] COMPOSITIONS HAVING USE AS TREATMENT OF NEUROPSYCHIATRIC DEFICITS

[75] Inventors: Peter Bridge, Washington, D.C.; Frederick K. Goodwin, Chevy Chase, Md.

[73] Assignee: The United States of Americas as represented by the Department of Health and Human Services, Washington, D.C.

[21] Appl. No.: 352,313

[22] Filed: May 16, 1989

Related U.S. Application Data

[63] Continuation-in-part of Ser. No. 285,559, Dec. 16, 1988, which is a continuation-in-part of Ser. No. 199,873, May 27, 1988, abandoned.

[51] Int. Cl.$^5$ .................. A61K 37/02; C07K 7/08
[52] U.S. Cl. ........................................ 514/16; 514/15; 514/17
[58] Field of Search .................. 514/16, 17, 15

[56] References Cited

U.S. PATENT DOCUMENTS 4,596,795 6/1986 Pitha ........................ 514/58
4,659,696 4/1987 Hirai et al. .................... 514/17

FOREIGN PATENT DOCUMENTS 0249390 12/1987 European Pat. Off. .......... 530/329
0249394 12/1987 European Pat. Off. .......... 530/329

OTHER PUBLICATIONS

Pert, C., et al., Psychopharmacology Bull., 24(3):315-319, 1988.
Pert, C. et al., Ann. Neurol., 23(Suppl.): S71-S73, 1988.
Brenneman, D., et al., Drug Development Research, 15:361-369, 1988.
Pert, C., et al., Proc. Natl. Acad. Sci, U.S.A., 83:9254-9258, Dec. 1986.
Ruff, M., et al., FEBS Letters, 211(1):17-22, Jan. 1987.
Berger, J., *AIDS: Modern Concepts & Therapeutic Challenges*, pp. 263-283, 1987.
Joy et al., Cerebral infarction following herpes zoster: The enlarging clinical spectrum, Neurology, Dec. 1989, pp. 1640-1641.
Gotham et al., 'Frontal' Cognitive Function in Patients with Parkinson's Disease 'on' and 'off' Levodopa, Brain 1988, pp. 299-321.
Starkstein et al., Depression and Cognitive Impairment in Parkinson's Disease, Brain 1989, pp. 1141-1153.
Ala et al., GM-1 Treatment of Alzheimer's Diease, Arch Neurol, vol. 47, Oct. 1990, pp. 1126-1130.
Taylor et al., Parkinson's Disease, Brain, 1987, pp. 35-51.

*Primary Examiner*—Howard E. Schain
*Assistant Examiner*—Susan M. Perkins
*Attorney, Agent, or Firm*—Cushman, Darby & Cushman

[57] ABSTRACT

The present invention relates to methods of treating mental disorders and memory deficits not caused by HIV infection. The methods involve administration of a thymoleptic effective amount of defined linear peptides to patients. The peptides can be administered for example, as a powder or a solution obtained by dissolving a powder in a pharmaceutically acceptable solvent.

11 Claims, No Drawings

COMPOSITIONS HAVING USE AS TREATMENT OF NEUROPSYCHIATRIC DEFICITS

This patent application is a continuation-in-part of U.S. Ser. No. 07/285,559, now pending, filed Dec. 16, 1988, which is a continuation-in-part of U.S. Ser. No. 07/199,873, filed May 27, 1988, now abandoned.

Peptides which inhibit binding of human immunodeficiency virus (HIV) to receptor sites on the cell surface have now been shown to be useful as agents for treatment of psoriasis and neuropsychiatric disorders, including memory deficit and mood disorders. Compositions formulated for administration by sublingual and nasal route have proven particularly useful.

BACKGROUND OF THE INVENTION

The use of the peptides of the formula:

$$R^a-Ser-Thr-Thr-Thr-Asn-Tyr-R^b \quad (I)$$

where $R^a$ represents an amino terminal residue Ala— or D—Ala and $R^b$ represents a carboxy terminal residue —Thr or —Thr amide or a derivative thereof with an additional Cys— residue at one or both of the amino and carboxy terminals, or a peptide of formula $$R^1-R^2-R^3-R^4-R^5 \quad (II)$$

where $R^1$ is an amino terminal residue Thr—, Ser—, Asn—, Glu—, Arg—, Ile— or Leu—,
$R^2$ is Thr, Ser or Asp,
$R^3$ is Thr, Ser, Asn, Arg, Gln, Lys or Trp
$R^4$ is Tyr
and $R^5$ is preferably a carboxy terminal residue —Thr, —Arg, or—Gly or a derivative thereof with a corresponding D-amino acid as the amino terminal residue, and/or a corresponding amide derivative at the carboxy terminal residue and/or additionally a Cys-residue at one or both of the amino and carboxy terminals have been disclosed by Pert, et al (U.S. patent application Ser. No. 07/048,148). These short peptides inhibit binding of human immunodeftciency virus (HIV) to human cells by blocking receptor sites on the cell surface.

The realization that viruses may exert cell and tissue tropism by attachment at highly specific sites on cell membrane receptors has encouraged investigators to seek agents which would bind at the viral receptor sites of cell membranes, thus preventing binding of a specific virus to these cells. A demonstration of specific receptor-mediated vaccinia virus infectivity being blocked by synthetic peptides has been previously demonstrated (Epstein et al, Nature 318:663–667).

The HIV virus has been shown to bind to a surface molecule known as the CD4 or OKT4 region, which is present on various cells susceptable to HIV infection, including T lymphocytes and macrophages (see Shaw et al, Science 226:1165–1171 for a discussion of tropism of HIV-III).

In addition to symptoms arising from immunodeficiency, patients with AIDS show neuropsychological deficits. The central nervous and immune systems share a large number of specific cell-surface recognition molecules, serving as receptors for neuropeptide-mediated intercellular communication. The neuropeptides and their receptors show profound evolutionary stability, being highly conserved in largely unaltered form in unicellular organisms as well as higher animals. Furthermore, the central nervous and immune systems show common CD4(OKT4) cell-surface recognition molecules which serve as receptors for the binding of HIV envelope glycoprotein (gp 120). Since the same highly conserved neuropeptide informational substances integrate immune and brain function through receptors remarkably similar to those of HIV, it was postulated a very similar amino acid sequence between the HIV glycoprotein gp 120 and a short peptide previously identified in another context from the envelope region of the Epstein Barr-Virus might indicate the core peptide essential for viral receptor binding. It was postulated that such a peptide would be useful in preventing infection of new cells in patients suffering from AIDS, since it was believed the peptides would bind with receptor cells and block the binding of HIV gp 120, that such peptides binding to the receptor cites would give rise to production of antibodies directed to the peptide sequence, and that these peptides might be used to provide immunological basis for prevention of AIDS.

DESCRIPTION OF THE INVENTION

In view of the state of the art and the unexpected discoveries disclosed herein, it is the purpose of this invention to provide peptidecontaining compositions for use in treatment of chronic disease conditions such as neuropsychiatric disorders and psoriasis.

The present invention as disclosed provides means of treating psoriasis and neuropsychiatric disorders, including memory deficit and mood disorder by administration of the peptides of formulas I and II. Also disclosed herein are new compositions of matter which are especially useful when long-term treatment is required.

Studies were initiated in human subjects to evaluate the efficacy of peptides of Pert in treatment of AIDS patients for purposes of obtaining FDA approval. Among the human subjects tested were individuals suffering from psoriasis. In many patients the psoriasis was AIDS-related. However, some patients were suffering from psoriasis which was *not* AIDS related. These patients were among subjects used as controls. These subjects were found to respond very favorably to treatment with compositions of the invention.

Several of the control subjects also suffered from neuropsychiatric disorders which were not AIDS related. While these peptides were under evaluation for use in treating AIDS, it was found that patients who tested negative for antibodies to HIV, but who suffered from dementias and/or prior mood disorders showed significant improvement while receiving peptide therapy. While it had previously been known that AIDS patients' general sense of well-being improved during treatment with these peptides, it is now known that these peptides possess thymoleptic properties which are not associated with blocking infectivity of HIV.

Most interesting of all responses to these peptides has been the improvement seen in patients who have shown memory deficits. In view of these findings, the use pharmaceutical preparations of compounds of Formula I and Formula II in treatment of learning disabilities resulting from memory deficit is a particularly important aspect of the invention. Pharmaceutical compositions would also be useful as a means of in increasing memory in the elderly suffering from memory deficit and dementias of old age such as Alzheimer's disease.

The class of compounds for use in the practice of the invention contain peptides of the formula $$R^a\text{—Ser—Thr—Thr—Thr—Asn—Tyr—}R^b \quad (I)$$

wherein $R^a$ represents an amino terminal residue which is Ala—, D—ala, or Cys—Ala,
$R^b$ represents a carboxy terminal Thr—, Thr—amide, Thr—Cys or Thr—Cys—amide,
and derivatives thereof, such as esters and amides or a linear peptide formula:

$$R^1\text{—}R^2\text{—}R^3\text{—}R^4\text{—}R^5 \quad (II)$$

wherein $R^1$ is an amino terminal residue which is X—R' or R' wherein R' is Thr—,Ser—,Asn—,-Leu—,Ile—,Arg—or Glu— and X is Cys;
$R^2$ is Thr, Ser, or Asp;
$R^3$ is Thr, Ser, Asn, Arg, Gln, Lys or Trp;
$R^4$ is Tyr; and
$R^5$ is a carboxy terminal amino which is R"X or R" wherein R" may be any amino acid (Thr, Arg or Gly being preferred) or a linear peptide of the formula (III):

$$R^{1'}\text{—}R^2\text{—}R^3\text{—}R^4\text{—}R^{5'}$$

wherein R' is an amino terminal residue Ala—$R^1$ D—Ala—R' or X—Ala—R'
$R^{5'}$ is a carboxy terminal residue Thr, Thr amide or Thr—Cys; and derivatives thereof (preferably the amides and esters of the acids) or the physiologically acceptable salts thereof.

Wherein the abbreviations used have the following meanings:

| Amino Acid | Three Letter Code | One Letter Code |
|---|---|---|
| arginine | arg | R |
| asparagine | asn | N |
| aspartic acid | asp | D |
| cysteine | cys | C |
| glycine | gly | G |
| serine | ser | S |
| threonine | thr | T |
| tyrosine | tyr | Y |

Most preferred peptides as well as peptide T above, are octapeptides of formula (I):

D—Ala—Ser—Thr—Thr—Thr—Asn—Tyr—Thr and

D—Ala—Ser—Thr—Thr—Thr—Asn—Tyr—Thr—amide and the following pentapeptides of formula (II):

Thr—Asp—Asn—Tyr—Thr

Thr—Thr—Ser—Tyr—Thr

Thr—Thr—Asn—Tyr—Thr and their analogues with D-thr as the amino terminal residue and/or an amide derivate at the carboxy terminal.

The compounds of the invention may be benefically modified by methods known to enhance passage of molecules across the blood-brain barrier. Acetylation has proven to be especially useful for enhancing binding activity of the peptide. The terminal amino and carboxy sites are particularly preferred sites for modification.

These peptides may also be modified in a constraining conformation to provide improved stability and oral availability.

The peptides were custom synthesized by Peninsula Laboratories under a confidentiality agreement between the inventors and the manufacturer. The Merrifield method of solid phase peptide synthesis was used. (See U.S. Pat. No. 3,531,258 which is incorporated herein by reference.) The synthesized peptides are especially preferred. While Peptide T and the pentapeptide which is a portion thereof could be isolated from the virus, the peptides prepared in accord with Merrifield are free of viral and cellular debris. Hence, untoward reactions to contaminants does not occur when the synthesized peptides are used.

The peptides of the invention may be produced by any conventional method of peptide synthesis. Both solid phase and liquid phase methods may be used. We have found the solid phase method of Merrifield to be particularly convenient. In this process the peptide is synthesized in a stepwise manner while the carboxy end of the chain is covalently attached to the insoluble support. During the intermediate synthetic stages the peptide remains in the solid phase and therefore can be conveniently manipulated. The solid support was a chloromethylated styrene-divinylbenzene copolymer.

An N-protected form of the carboxy terminal amino acid, e.g., a t-butoxycarbonyl protected (Boc-) amino acid, is reacted with the chloromethyl residue of the chloromethylated styrene divinylbenzene copolymer resin to produce a protected amino acyl derivative of the resin, where the amino acid is coupled to the resin as a benzyl ester. This is deprotected and reacted with a protected from of the next required amino acid thus producing a protected dipeptide attached to the resin. The amino acid will generally be used in activated form, e.g., by use of a carbodiimide or active ester. This sequence is repeated and the peptide chain grows one residue at a time by condensation at the amino end with the required N-protected amino acids until the required peptide has been assembled on the resin. The peptide-resin is then treated with anhydrous hydrofluoric acid to cleave the ester linking the assembled peptide to the resin, in order to liberate the required peptide. Side chain functional groups of amino acids which must be blocked during the synthetic procedure, using conventional methods, may also be simultaneously removed. Synthesis of a peptide with an amide group on its carboxy terminal can be carried out in any conventional manner, using a 4-methylbenzhydrylamine resin.

Pharmaceutical compositions comprising a peptide compound of the invention in association with a pharmaceutically acceptable carrier or excipient are appropriate for administration as thymoleptic agents or for use in treatment of psoriasis. Such compositions may be presented for use in any conventional manner in admixture with one or more physiologically acceptable carriers or excipients.

Thus, the peptides according to the invention may be formulated for oral, buccal, parenteral, topical, or rectal administration.

Peptides may also be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile, pyrogen-free water, before use.

The pharmaceutical compositions according to the invention may also contain other active ingredients such as antimicrobial agents, or preservatives.

A preferred route for use in practice of the inventive method is nasal inhalation ("snorting"). However, any means which provides ready bio-availability without injection would be advantageous, for example, buccal or sublingual administration. Buccal preparations prepared according to the method of Pitha (U.S. Pat. No. 4,727,064 which is incorporated herein by reference) would be appropriate. However, since it appears these small peptides are not destoryed in the intestinal tract, the means of administration of such peptides for the inventive method is not confined to the preferred means recited.

Particularly preferred compositions of the invention are compositions for intranasal administration. The peptides may be presented as lyophylized powders prepared with or without filler. Formulations were prepared which contained manmitol. Other preparations lacked such additives. The lyophilized powders were prepared in vials containing appropriate dosage. When the vial was broken open the patient would "snort" the contents of the vial.

The powders may also be dissolved and administered by nasal spray. The solutions of 1 mg/ml to 25 mg/ml were used at dosages of 1.2–30 to 10 mg/day for adults.

logical Battery, is a sensitive measure of general brain functions, and requires the subject to connect randomly placed letters and numbers in correct alternate sequence (e.g., 1-A-2-B-3-C, etc.). Alternate versions of Trails B were used. This test involves recognition of the symbolic significance of letters and numbers, visual scanning, psychomotor speed, and complex cognitive sequencing or double conceptual tracking.

2. PASAT (Paced Auditory Serial Addition Test): An assessment of an individual's ability for attention, for shifting cognitive set, and for mathematical abilities. It requires basic educational skills to test mathematical ability. The PASAT requires that the subject add 60 pairs of randomized digits so that each is added to the one immediately preceding it. The digits are presented via audiotape and are organized into 4 blocks which vary in rate of digit presentation: Block 1, 2.4 sec rate; Block 2, 2.0 sec rate; Block 3, 1.6 sec rate; Block 4, 1.2 sec rate. This test is an extremely sensitive measure of deficits in information processing ability since it requires complex sustained attention and perseverance of attention and speed. It has been found to be a sensitive measure of recovery in post-concussion patients. An individual had a history of mild psoriasis which, by personal choice, has been treated with only topical treatments including hydrocortisone, coal tar derivatives, and calamine lotion. During a one month period follow-up subsequent to testing, the lesions in question did not return, nor did new lesions appear.

No evidence of either CNS or immunologic toxicity associated with drug administration was observed in any of the patients or in any of the normal volunteers.

The activity of these peptides on neuropsychiatric signs and symptoms is illustrated in Table 1.

| | | CLINICAL EFFECTS OF PEPTIDE T IN NORMAL VOLUNTEER SUBJECTS | | | | | | | |
|---|---|---|---|---|---|---|---|---|---|
| PAT # | CLIN. HISTORY | PEPTIDE DOSAGE | TRAILS B | PASAT | WECHSLER MEM | CVLT | BECK | SPEILBERGER | POMS |
| 1 | Alcohol abuse | 0.033–0.133 mg/kg | + | + | + | + | + | + | + |
| 2 | Poly-drug abuse | 0.033–0.133 mg/kg | + | + | + | + | + | + | + |
| 3 | Dys-lexia | 0.033–0.133 mg/kg | + | + | + | + | − | − | + |
| 4 | Depression | 0.033–0.133 mg/kg | − | − | + | + | − | − | + |
| 5 | Depression | 0.033–0.133 mg/kg | + | + | + | − | + | + | + |
| 6 | No NP | 0.033–0.133 mg/kg | + | − | − | − | − | − | + |

At these dosages, no toxic effects were observed. Each dose consists of 4 puffs. Using a preferred method of administration the patients alternate nostrils with each puff. When the preparation was refrigerated, the solution appeared to thicken. However, warming the vial to room temperature for one to two days resulted in clearing of the solutions. When compositions are to be used more immediately, the contents can be warmed by rolling the vial between the hands, then shaking vigorously a few times to liquify the contents. The tests administered are described below:

1. Trails B: A test of attention and cognitive flexibility. Trails B, a part of the Halstead-Reitan Neuropsycho- 3. Wechsler Memory: An assessment of modality-specific memory deficits, the test has both a logical and a visual component. The improved scores on the subjects were in the logical or memory scores based on ability to recall detail of a story that has two versions, thus allowing a pre- and post-drug testing assessment. Improvement is judged by changes in scores of one standard deviation compared to age appropriate norms.

4. CVLT (California Verbal Learning Test): The CVLT provides a brief, sensitive assessment of the amount of impairment in memory and learning as well as specifying the strategies and processes involved in different forms of memory failure. It has been used in the diagnosis and treatment of memory impairments secondary to neurological disorders and psychiatric problems. The CVLT evaluates an individual's ability to learn a list of words over five trails, to learn a second interference list, free and cued recall of the first list over a short- and long-delay, and recognition. Quantitative measures of eleven different areas of memory and learning are provided, along with normative data for each. Scores that differ one or more standard deviations from the age appropriate average are considered significant. There are two versions of this test allowing assessments both at baseline and at post-test. Subjects showed an increased ability on long delay recall on this test.

5. BECK Depression Scale: Clinical measure of depression, has accepted cut-off scores for clinically significant depression. The control subjects were the patients described as having prior histories of depression. They had elevated, but not clinically significant, scores on depression which improved on drug.

6. Spielberger Trait State Anxiety: A test of state anxiety measures both the individual's current anxiety state as well as general predisopsition to anxiety (trait).

7. POMS (Profile of Mood State): A six subscale self-report instrument of fatigue, vigor, depression, anxiety, anger, and confusion. The cases reported here show subjects with decreased fatigue and increased vigor scores. There was elevation of depression scores consistent with the BECK in three subjects. Otherwise, the range of scores on other scales was within the normal range. The test reports T scores where the baseline is 50 and variations are measured in standard deviations around that. Clinical significance reported here are changes in scores of one standard deviation or more.

As indicated in the Table, symptoms of substance abuse, childhood dyslexia and depression were ameliorated. The peptide having the formula:

D—Ala—Ser—Thr—Thr—Thr—Asn—Tyr—Thr—amide  (Formula A)

was given at dosage of 0.033 mg/kg/da to 0.133 mg/kg/da for seven days. As indicated in the Table, the unexpected effects observed in these volunteers who tested negative for HIV antibodies were the following:

1. Incremental scores on memory and attention components of standard neuropsychologic tests (e.g., Halstead-Reitan Trails B, Paced Auditory Serial Additon Test, Compex Figure Test, Wechsler Memory Test, California Verbal Learning Test) which remitted after Peptide T was discontinued.

2. Improved mood scores on depression scales in the two research volunteers who had prior histories of depression. This effect maintained for one month of follow-up.

All subjects reported decreased fatigue and increased energy and vigor. This effect abated off drug.

All subjects were observed to demonstrate increases in physical activity while on drug, which did not continue after drug discontinuance.

These CNS manifestations of Peptide T were independent of any immunologically mediated effects on lymphocyre subet count, mitogen stimulation, or natural killer activity.

It was postulated that affinity constants similar to those for morphine would be operative. On this basis, dosage of 0.0003 mg/kg/da to 0.33 mg/kg/da was chosen. The daily dosage may preferably be given in one to four increments.

PREPARATION OF COMPOSITIONS

A. A mixture containing 1200 ml 2.5% mannitol and 3.56 grams of a peptide preparation containing 91.7% peptide of formula A was mixed well. The mixture was adjusted to pH 6.15. The solution was filtered through a 0.22 micron Durapor ® filter and the sterilized solution was delivered by a peristalic pump in 2 ml aliquates into sterile 5 ml serum vials. The vials were stoppered and transferred to the freeze drier. After drying was accomplished, the vials were sealed. Vials could be stored under freezing conditions for several months.

B. Distilled water (768 ml) was added to 9.9 grams of a peptide preparation supplied by Peninsula which contained 97% peptide of formula A. The powdered peptide product was very light and very static. The solution was covered and sonicated until dissolved (4–6 hours). The solution was then transferred to a silo filtering apparatus and filtered through a 0.22 micron Durapore ® filter membrane into a sterile receptacle. The sterile solution was dispensed into vials and dried in the manner previously described.

For administration by injection or infusion, the daily dosage employed for treatment of an adult human of approximately 70 kg body weight will range from 0.2 mg to 10 mg, preferably 0.5 to 5 mg, which may be administered in 1 to 4 doses, for example, depending on the route of administration and the condition of the patient.

For administration nasally or sublingually somewhat higher dosage will be needed. For the human adult of about 70 kg, 5–50 mgm may be given one to four times a day.

What we claim is:

1. A method of treating mental disorders not caused by HIV infection which comprises administration of a thymoleptic effective amount of (1) a linear peptide of the formula:

$$R^a-Ser-Thr-Thr-Thr-Asn-Tyr-R^b \quad (I)$$

wherein $R^a$ represents an amino terminal residue which is

Ala—,D—Ala, or Cys—Ala—, $R^b$ represents a carboxy terminal Thr-, Thr-amide, Thr-Cys or Thr-Cys-amide, and derivatives thereof which are esters and amides; (2) a thymoleptic effective amount of a linear peptide formula:

$$R^1-R^2-R^3-R^4-R^5 \quad (II)$$

wherein
  $R^1$ is an amino terminal residue which is X-R' or R' wherein R' is Thr—,Ser—,Asn—,Leu,Ile—,Arg— or Glu— and X is Cys;
  $R^2$ Thr, Ser, or Asp;
  $R^3$ is Thr, Ser, Asn, Arg, Gln, Lys or Trp;
  $R^4$ is Tyr; and $R^5$ is a carboxy terminal residue which is R"X or R" wherein R" may be any amino acid and X is Cys; or (3) a thymoleptic effective amount of a linear peptide of the formula:

$$R^{1\prime}-R^2-R^3-R^4-R^{5\prime} \qquad (III)$$

wherein $R^{1\prime}$ is an amino terminal residue Ala-R', D-Ala-R' or X—Ala—R', R', $R^2$, $R^3$, $R^4$ and X are defined as above, and $R^{5\prime}$ is a carboxy terminal residue Thr, thr amide or Thr-Cys; and ester and amide derivatives thereof or the physiologically acceptable salts thereof.

2. A method of claim 1 wherein the peptide is of the formula:

D—Ala—Ser—Thr—Thr—Thr—Asn—Tyr—Thr—amide

3. A method of claim 1, wherein the composition administered is a cyclodextrin inclusion complex.

4. A method of claim 1, wherein the composition administered is a lyophilized peptide preparation.

5. A method of claim 1, wherein the composition administered is adapted for sublingual or buccal administration.

6. A method of treating memory deficit not caused by HIV infection which comprises administration of an effective amount (1) of a linear peptide of formula:

$$R^a-Ser-Thr-Thr-Thr-Asn-Tyr-R^b \qquad (I)$$

wherein $R^a$ represents an amino terminal residue which is

Ala—, D—Ala, or Cys—Ala—, $R^b$ represents a carboxy terminal Thr—, Thr—amide, Thr—Cys or Thr—Cys—amide, and derivatives thereof which are esters and amides; or (2) a thymoleptic effective amount of a linear peptide of formula:

$$R^1-R^2-R^3-R^4-R^5 \qquad (II)$$

wherein $R^1$ is an amino terminal residue which is X—R' or R' wherein R' is Thr—,Ser—,Asn—,Leu,Ile—,Arg— or Glu— and X is Cys;

$R^2$ is Thr, Ser, or Asp;

$R^3$ is Thr, Ser, Asn, Arg, Gln, Lys or Trp;

$R^4$ is Tyr; and $R^5$ is a carboxy terminal residue which is R"X or R" wherein R" may be any amino acid and X is Cys; or (3) a thymoleptic effective amount of a linear peptide of the formula:

$$R^{1\prime}-R^2-R^3-R^4-R^{5\prime} \qquad (III)$$

wherein $R^{1\prime}$ is an amino terminal residue Ala—R', D—Ala—R' or X—Ala—R', R', $R^2$, $R^3$, $R^4$ and X are defined as above, and $R^{5\prime}$ is a carboxy terminal residue Thr, thr amide or Thr-Cys; and ester and amide derivatives thereof or the physiologically acceptable salts thereof.

7. The method according to claim 6 wherein said peptide is administered as a powder or a solution obtained by dissolving a powder in a pharmaceutically acceptable solvent.

8. The method according to claim 1 wherein said administered peptide is of formula $$R^a-Ser-Thr-Thr-Thr-Asn-Tyr-R^b \qquad (I)$$

wherein $R^a$ represents an amino terminal residue which is

Ala—, D—Ala, or Cys—Ala—, $R^b$ represents a carboxy terminal Thr—, Thr—amide, Thr—Cys or Thr—Cys—amide, or an ester or amide derivative thereof.

9. The method according to claim 1 wherein $R^5$ of said peptide II is Thr, Arg or Gly.

10. The method according to claim 6 wherein said administered peptide is of formula:

$$R^a-Ser-Thr-Thr-Thr-Asn-Tyr-R^b \qquad (I)$$

wherein $R^a$ represents an amino terminal residue which is

Ala—, D—Ala, or Cys—Ala—, $R^b$ represents a carboxy terminal Thr—, Thr—amide, Thr—Cys or Thr—Cys—amide, or an ester or amide derivative thereof.

11. The method according to claim 6 wherein $R^5$ of said peptide II is Thr, Arg or Gly.

* * * * *